United States Patent [19]

Sewell, Jr.

[11] Patent Number: 5,131,379
[45] Date of Patent: Jul. 21, 1992

[54] DEVICE AND METHOD FOR INSERTING A CANNULA INTO A DUCT

[76] Inventor: Frank K. Sewell, Jr., 1413 N. Elm St., Henderson, Ky. 42420

[21] Appl. No.: 647,042

[22] Filed: Jan. 29, 1991

[51] Int. Cl.$^5$ .................................................. A61B 1/00
[52] U.S. Cl. ......................................... 128/4; 606/108; 606/159; 606/205
[58] Field of Search ............... 606/108, 150, 205–209, 606/46, 51, 52, 159, 167; 128/4–8, 207.29; 604/157, 164, 95

[56] References Cited

U.S. PATENT DOCUMENTS

| | | | |
|---|---|---|---|
| 1,303,135 | 5/1919 | Wappler | 128/7 |
| 2,068,721 | 1/1937 | Wappler et al. | 606/46 |
| 3,314,431 | 4/1967 | Smith, Jr. | 606/108 |
| 4,245,624 | 1/1981 | Komiya | 128/4 |
| 4,411,653 | 10/1983 | Razi | 606/108 |
| 4,501,274 | 2/1985 | Skjaerpe | 606/167 |
| 4,538,594 | 9/1985 | Boebel et al. | 128/6 |
| 4,559,041 | 12/1985 | Razi | 128/207.29 |
| 4,653,476 | 3/1987 | Bonnet | 128/4 |
| 4,706,655 | 11/1987 | Krauter | 128/4 |
| 4,870,951 | 10/1989 | Suzuki | 128/4 |
| 4,889,118 | 12/1989 | Schwiegerling | 606/108 |
| 4,944,741 | 7/1990 | Hasson | 606/206 |
| 4,947,828 | 8/1990 | Carpenter et al. | 128/6 |
| 5,020,514 | 6/1991 | Heckele | 128/4 |

FOREIGN PATENT DOCUMENTS 2133696  8/1984  United Kingdom ............... 128/4

*Primary Examiner*—C. Fred Rosenbaum
*Assistant Examiner*—Ron Stright
*Attorney, Agent, or Firm*—Baker & Daniels

[57] ABSTRACT

Device for inserting a cannula into a duct. The device includes a housing having a handle and a distal end, the distal end being insertable through a laparoscopic trocar. Attached to the distal end is a duct alignment mechanism and a pivotable endoscope. The endoscope has a visualization capability and a cannula introduction channel and is pivotable between a retracted position in which the terminal end is generally parallel to the distal end of the housing and an extended position in which the terminal end is positioned such that a cannula extended from the cannula introduction channel is generally coaxial with a duct aligned by the duct alignment mechanism.

13 Claims, 3 Drawing Sheets

5,131,379

DEVICE AND METHOD FOR INSERTING A CANNULA INTO A DUCT

FIELD OF THE INVENTION

This invention relates to devices and methods useful for inserting a cannula into a duct or vessel of an individual, and in particular, a device and method suitable for use during endoscopic surgery.

BACKGROUND OF THE INVENTION

The required recovery period following surgery is often directly proportional to the size of the incision(s) made during surgery. Accordingly, laparoscopic surgery, which typically requires that only several small (1 cm.) incisions be made, is an increasingly utilized form of surgery because the recovery period is significantly reduced. Because the incisions made for laparoscopic surgery are very small, manipulation of the surgical instruments in the body through the incisions is a very difficult and precise task. For example, when performing a laparoscopic cholecystectomy, a cholangiogram is usually performed. Conventional procedure, as noted in Reddick and Olsen, *Manual of Laparoscopy for the General Surgeon*, requires that, operating through a 1 cm. incision, a cut be made halfway through the cystic duct, and that a cholangiocatheter be inserted at an angle in the partial cut of the cystic duct. However, it is extremely difficult to avoid completely severing the cystic duct when making the partial cut. If the cystic duct is severed, it will retract because it is under tension, and it may be impossible to perform the cholangiogram. Moreover, it is also extremely difficult to insert the cholangiocatheter into the cystic duct at an angle. Numerous attempts at insertion may injure surrounding tissue or sever the cystic duct. There are also many other surgical procedures which contemplate that a cannula or catheter be inserted to a duct or vessel in a similar manner, and which are equally difficult and dangerous to perform. These problems are not solved by known surgical instruments, such as those disclosed in U.S. Pat. Nos. 4,706,655, 4,653,476, 4,559,041, 4,411,653, 2,068,721, 4,245,624, 4,501,274, 4,889,118, 3,314,431, 1,303,135 and 4,870,951.

OBJECTS OF THE INVENTION

Accordingly, it is an object of the invention to provide a device and method for inserting a cannula into a vessel or duct.

It is a further object of the invention to provide a device and method that will automatically align a cannula with a vessel or duct.

It is a further object of the invention to provide a device and method that can sever and hold a vessel or duct, and keep it aligned for insertion of cannula.

It is a further object of the invention to provide a device for inserting a cannula into duct that may be used laparoscopically.

SUMMARY OF THE INVENTION

The invention is a device for inserting a cannula into a duct. The device includes a housing having a handle and a distal end, the distal end being insertable through a laparoscopic trocar. Attached to the distal end is a duct alignment means and a pivotable endoscope means. The endoscope has a visualization means and a cannula introduction means and is pivotable between a retracted position in which the terminal end is generally parallel to the distal end of the housing and an extended position in which the terminal end is positioned such that a cannula extended from the cannula introduction means is generally coaxial with a duct aligned by the duct aligment means.

DETAILED DESCRIPTION

In one embodiment, the invention comprises a modified surgical cutting gun. Such guns are presently used to completely sever ducts and vessels during surgery. However, the gun is modified in two respects. First, a set of forceps clamps is built into one side of the gun. The clamps themselves are near the tip of the gun, and the handles are near the back of the gun. Secondly, an endoscope, preferably of small diameter such as a pediatric endoscope manufacturered by Olympus, has been attached to the gun, and the end of the endoscope is attached to the tip of the gun by a pivotable hinge. A hinge point extends vertically through one side of the end of the endoscope. Therefore, when the back of the endoscope is pushed toward the end of the gun, the tip of the endoscope will pivot so its face is perpendicular to the tip of the gun.

In order to use the device, it is first placed through a trocar, and the j-tip of the gun is placed around the duct to be cut. The forcep clamps are then extended to grasp one side of the duct to keep it from retracting when the duct is cut. Trigger 25 of cutting gun, which is operatively connected to blade 24, is then pulled to sever duct 22. The unclamped half of the duct retracts because it is normally stretched, but this is of no concern for time being. The endoscope is then pushed toward the end of the gun. The tip of the endoscope is forced to pivot around the hinge by which it is connected to the gun, so that the tip of endoscope is directly facing the severed duct. Next, the cannula is pushed through the endoscope. Using the eyepiece of the endoscope to visualize the duct, it is very easy to manipulate the device so the cannula can be directly inserted into the duct. The cannula can then be used to, for example, to inject dye into the duct so an X-ray may be taken.

Figure 1:
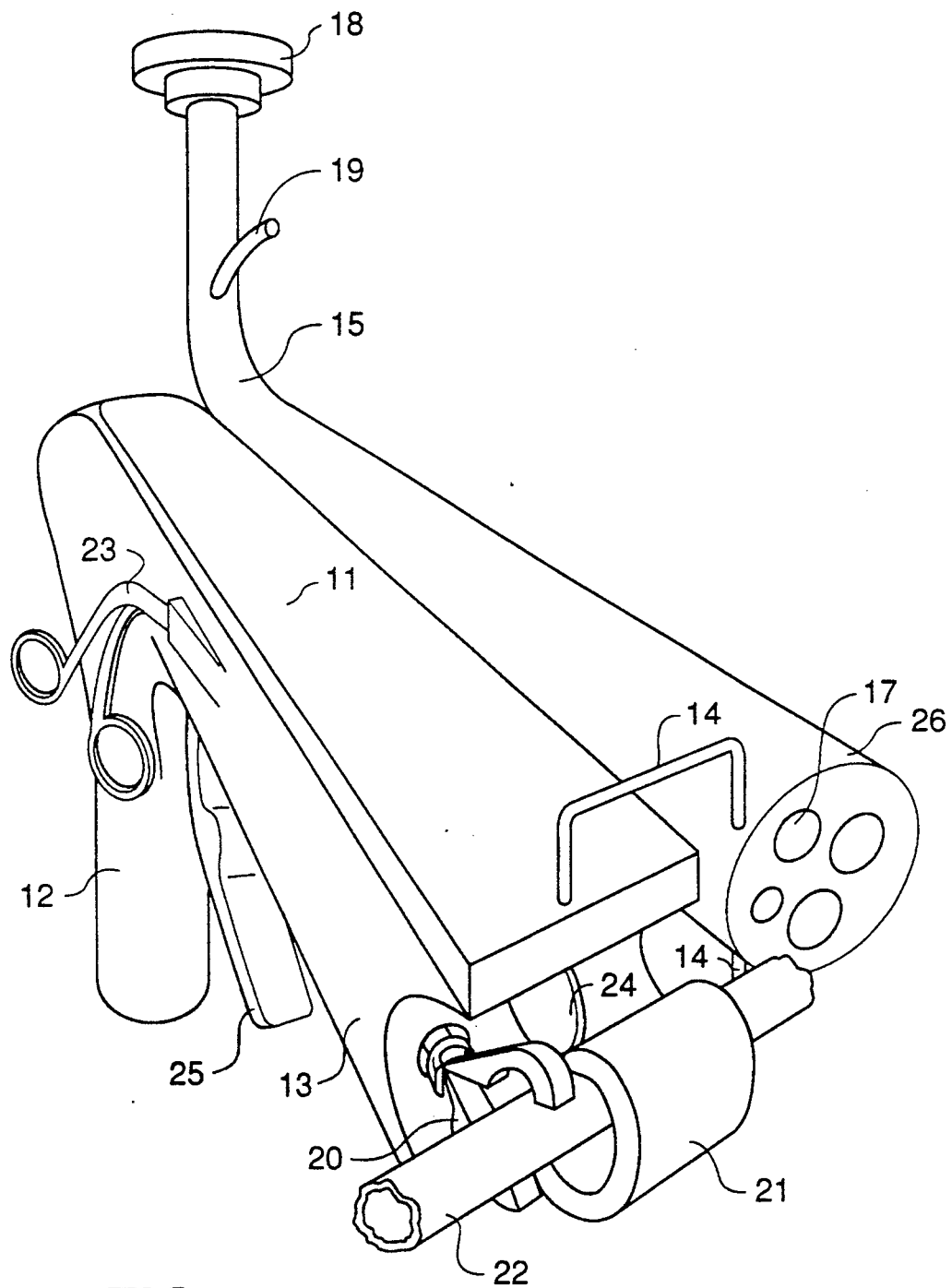
FIG. 1 is a perspective view showing one embodiment of a device of the present invention showing the endoscope in its retracted position.

Referring to FIG. 1, one embodiment of the device comprises housing 11 having a handle 12 and a distal end 13. Housing should be of sufficient lenth and diameter to allow it to be easily positioned and manipulated during endoscopic surgery. Housing 11 may comprise a modified surgical staple gun, for example an AUTOSUTURE powered disposable LDS stapler model 091451.

Attached to distal end 13 by hinge 14 is endoscope 15. This combination is of sufficiently narrow diameter to be passed through a laparoscopic trocar, and may be for, example, less than 1 cm. in diameter. Endoscope 15 may contain a number channels at terminal end 26, for example, a cannula introducing channel 16 and a visualization channel 17, which permit a surgeon to view a surgical procedure through eyepiece 18. Endoscope also includes upper port 19 into which a cannula may be inserted to be passed out of channel 16.

Housing 11 also includes J-shaped structure comprising a duct alignment means 21, which may be used to position the instrument with respect to duct 22. It should be understood that for the purposes of this application and the claims, "duct" is intended to include any other body organ with which the invention may be used, including the cystic duct and vessels. Housing also holds forcep clamps 20, which may be actuated by forceps handles 23 to grasp and hold duct 22. Housing also holds cutting blades 24, which when trigger 25 is squeezed, will sever duct 22. In one embodiment of the invention, pulling trigger 25 will also simultaneously apply a surgical staple to the side of the duct not clamped by clamps 20.

Figure 2:
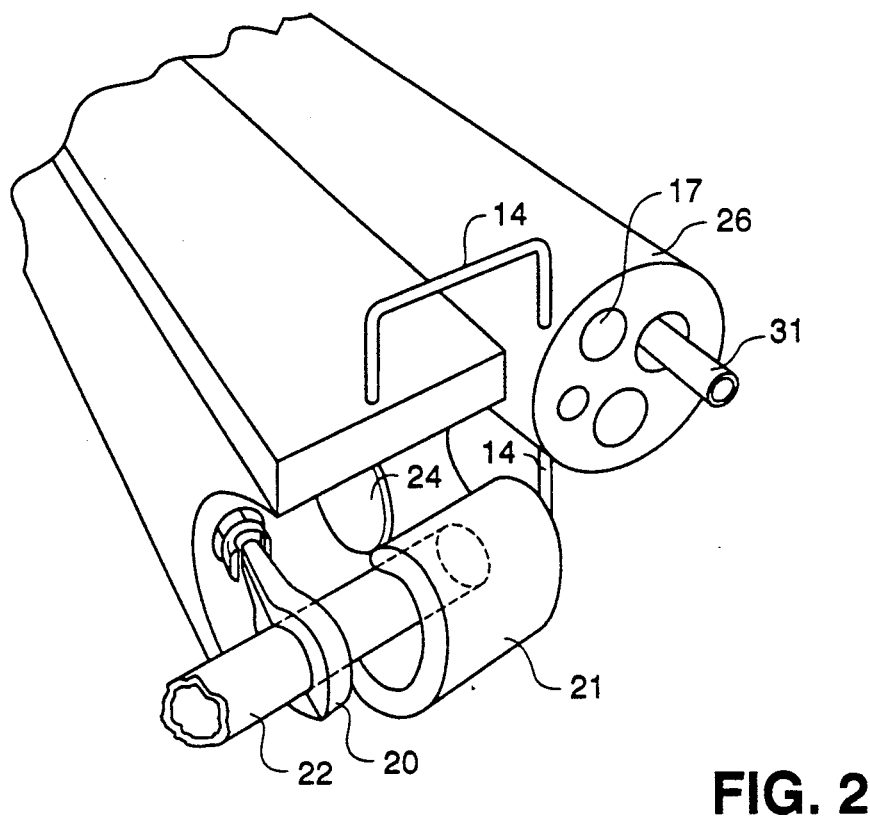
FIG. 2 is a perspective view showing the distal end of a device of the present invention aligning a duct into which a cannula is to be inserted.
Figure 3:
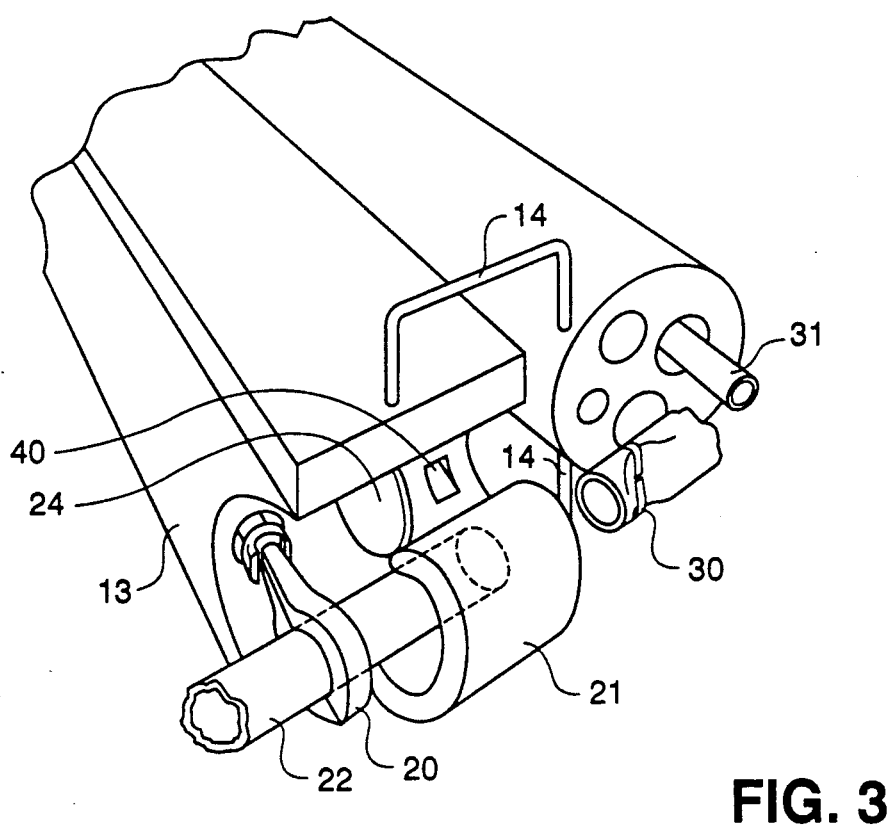
FIG. 3 is a perspective view showing the distal end of a device of the present invention after the duct has been cut and one side stapled.
Figure 4:
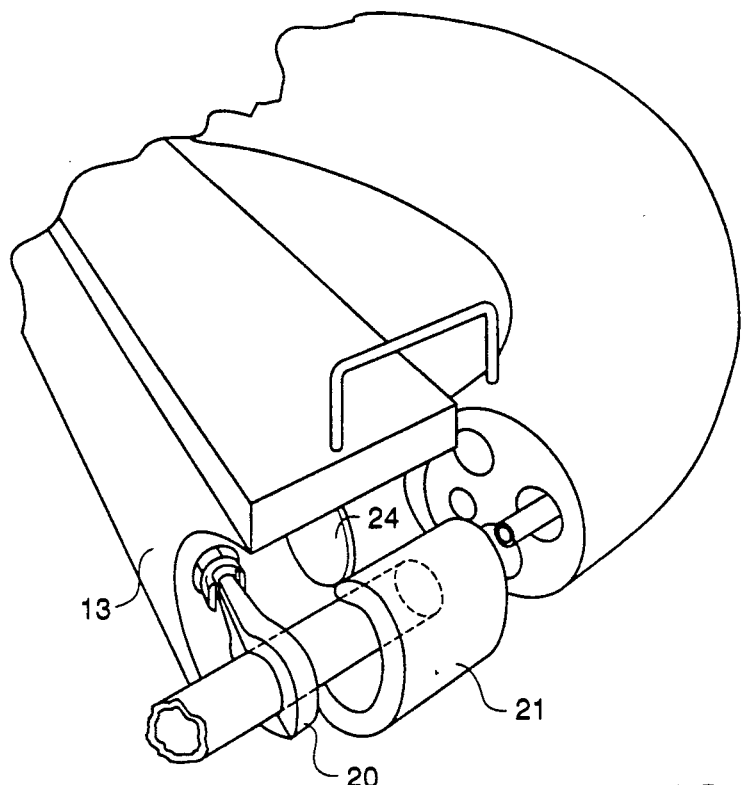
FIG. 4 is a perspective view showing the distal end of a device of the present invention showing the position of the endoscope after being moved to its extended position and alignment of the cannula with the duct.
Figure 5:
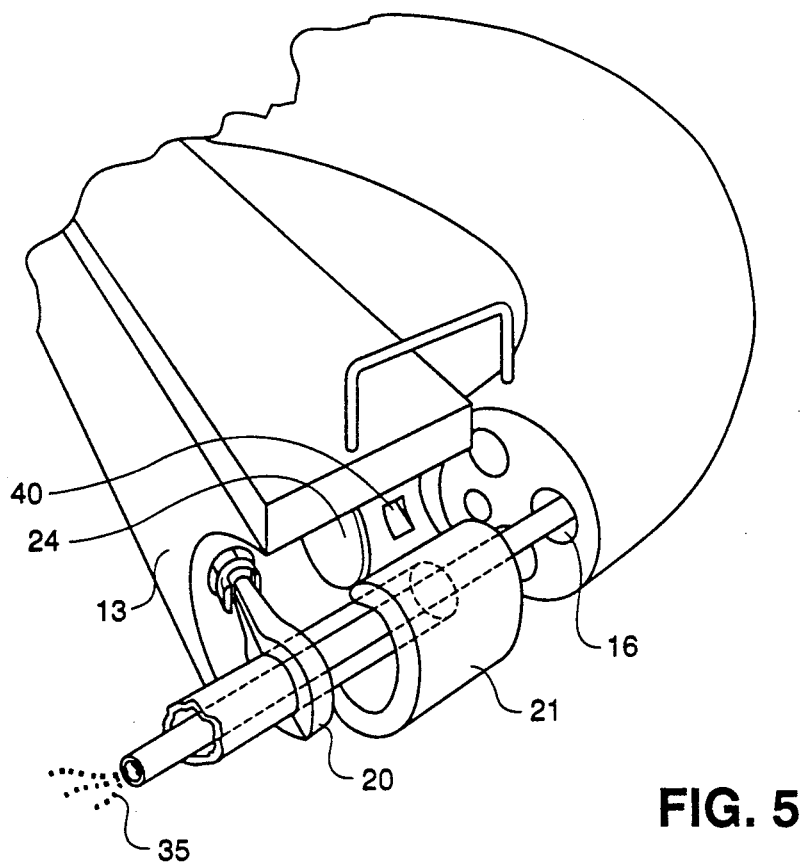
FIG. 5 is a perspective view showing the distal end of a device of the present invention showing insertion of the cannula into the duct.

In order to use the invention, J-shaped alignment means is placed around duct 22 into which the cannula is to be introduced. Forceps handles 23 are then moved to close clamps 20 around one side of the duct to the position shown in FIG. 2. If necessary, endoscope 15 may be manually pushed towards its terminal end 26, which will force terminal end 26 to pivot about hinge 14, to provide improved visualization of the alignment of duct 22 in alignment means 21. At this point, trigger 23 is pulled, and cutting blade 24 completely severs duct 22 and simultaneously applies a surgical staple 30 from hole 40 in housing distal end 13" to duct 22 as shown in FIG. 3. Depending on the duct being severed, the side of duct 22 to which the staple is applied may retract under its own tension. At this point, endoscope 15 may be manually pushed towards its terminal end 26 so that it moves from its retracted position in which terminal end 26 is generally parallel housing distal end 13 as shown in FIGS. 1–3, to its extended position shown in FIGS. 4 and 5. In the extended position, the cannula introducing channel 16 of endoscope 15 is generally coaxial with the axis of duct 22. Accordingly, cannula 31 may be inserted through endoscope port 19 and pushed until it exits cannula channel 16 as shown in FIGS. 2–5. Cannula 31 continues to be advanced, and at this point, the device may be slightly tilted and adjusted as necessary to precisely align cannula 31 with duct 22. At this point, cannula 31 is advanced to insert it directly into duct 22, preferably beyond the point where clamps 20 hold duct 22. Radiolucent dye 35 may then be injected through cannula 31 into the duct and a cholangiogram or other appropriate procedure undertaken.

It will be appreciated that the present invention allows insertion of a cannula into a duct using a very easy procedure which may be undertaken during laparoscopic surgery. Moreover, the instruments for visualizing, aligning, holding, cutting, stapling, and introducing a cannula into the duct are combined in a single unit. All elements may be moved simultaneously which significantly reduces time during surgical procedures.

I claim:

1. A device for inserting a cannula into a duct comprising:
    a housing having a handle and a distal end, the distal end insertable through a laparoscopic trocar,
    duct alignment means attached to the distal end,
    pivotable endoscope means attached to the distal end of the housing, the endoscope means comprising a terminal end having terminal end visualization means and a terminal end cannula introduction means, the terminal end being pivotable between a retracted position in which the terminal end is generally parallel to the distal end of the housing and an extended position in which the terminal end is positioned such that a cannula extending from the cannula introduction means is generally coaxial with a duct aligned by the duct alignment means.

2. The device of claim 1 wherein the terminal end of the endoscope may be pivoted from the retracted position to the extended position by pushing the endoscope toward the distal end of the housing.

3. The device of claim 1 wherein the alignment means comprise a J-shaped structure extending from the distal end of the housing.

4. The device of claim 1 further comprising clamp means extending from the distal end of the housing.

5. The device of claim 1 further comprising stapling means attached to the distal end of the housing for applying a staple to a duct aligned by the duct alignment means.

6. The device of claim 1 wherein the housing further comprises cutting means at its distal end for serving a duct aligned by the duct alignment means.

7. The device of claim 6 further comprising a trigger adjacent to the handle, the trigger being operatively connected to the cutting means.

8. A method for inserting a cannula into a duct, comprising the steps of:
    providing an endoscope means having a terminal end and pivotable between extended and retracted positions, a duct alignment means, a severing means, a cannula introduction means, a clamping means, a stapling means and a liquid injecting means,
    positioning the terminal end of the endoscope means in the retracted position,
    aligning the duct in the duct alignment means,
    severing that portion of the duct aligned by the duct alignment means moving the endoscope to the extended position,
    moving the cannula from the cannula introduction means into one of the severed ends of the duct.

9. The method of claim 8 further comprising the step of injecting a liquid into the duct through the cannula.

10. The method of claim 8 wherein the duct comprises a cystic duct.

11. The method of claim 8 further comprising the step of clamping one side of the severed duct before severing the duct.

12. The method of claim 11 further comprising the step of stapling the unclamped side of the duct.

13. The method of claim 12 wherein the stapling and severing steps are performed substantially simultaneously,

* * * * *